United States Patent [19]

Moldawer et al.

[11] Patent Number: 4,512,974

[45] Date of Patent: Apr. 23, 1985

[54] TREATMENT OF PROTEIN MALNOURISHED SURGICAL PATIENTS

[76] Inventors: Lyle L. Moldawer, 1 E. Quinobequin Rd., Waban, Mass. 02169; George L. Blackburn, 100 Memorial Dr., Cambridge, Mass. 02142; Bruce R. Bistrian, 189 Argilla Rd., Ipswich, Mass. 01938

[21] Appl. No.: 447,984

[22] Filed: Dec. 8, 1982

[51] Int. Cl.$^3$ .............................................. A61K 35/16
[52] U.S. Cl. ..................................... 424/101; 424/88
[58] Field of Search .................................. 424/101, 88

[56] References Cited

PUBLICATIONS

Kampschmidt et al., J. Reticulo endothelial Soc., Mar. 1975, pp. 162–169.
Hoffman–Goetz et al., J. Physiol. vol. 295, (1979) pp. 419–430.
Hoffman–Goetz et al., Am. J. Clinical Nutr. vol. 32, (Jul. 1979), pp. 1423–1427.
Hoffman–Goetz et al., Am J. Clinical Nutrit., vol. 34, (Jun. 1981), pp. 1109–1116.
Harvey et al., Am. J. Clinical Nutrit., vol. 34, (Oct. 1981), pp. 2013–2022.
Keenan et al., J. Lab. & Clin. Med., vol. 100, (Dec. 1982), pp. 844–857.
Hardy et al., Hardy's Textbook of Surgery (1983), pp. 240–244.
Clowes et al., New England J. Med. vol. 308, No. 10, (Mar. 10, 1983), pp. 545–552.
Baracos et al., New Eng. J. Med. vol. 308, No. 10 (Mar. 10, 1983), pp. 553–558.
Beisel, New Eng. J. Med., vol. 308, No. 10 (Mar. 10, 1983), pp. 586–587.
Powanda et al., Am. J. Clinical Nutrit., vol. 35, (Apr. 1982), pp. 762–768.
Dinarello et al., Chem. Abst. vol. 95, (1981) pp. 113, 212a.
Chem. Abst. General Subject Index, 10th Collective, vol. 86–95, (1977–1981), p. 13929GS.

*Primary Examiner*—Sam Rosen
*Attorney, Agent, or Firm*—Donald Brown

[57] ABSTRACT

Exogenous LEM (Leukocyte Endogenous Mediator, also referred to as endogenous pyrogen) is parenterally administered to humans who are protein malnourished and are to undergo surgery, in order to preinitiate and then maintain the normal metabolic responses to the tissue damage occurring during surgery, and thereby promote the normal metabolic response by the human (patient).

10 Claims, No Drawings

TREATMENT OF PROTEIN MALNOURISHED SURGICAL PATIENTS

BACKGROUND OF THE DISCLOSURE

Major surgery on the human body causes many effects including severe tissue damage. It has been found that well-nourished normal patients who have undergone surgery should normally produce metabolic responses to the tissue damage. These metabolic responses tend to alleviate the symptoms associated with such tissue damage and in particular enhance the body's ability to promote wound healing and limit tissue damage at the site of surgery.

There are large numbers of people who undergo surgery but have substantially diminished capability to produce the normal metabolic responses to such surgical tissue damage. These individuals are generally those who are protein malnourished and surprisingly constitute a substantial portion of those patients who undergo surgery. Protein malnourished patients are normally considered as those having a serum albumin level of less than about 3.2 gm/dl (100 ml).

With the present invention it is now possible to provide parenteral therapy to such humans (patients), prior to the surgical procedure and for a period thereafter, to first preinitiate and then maintain the normal metabolic response which would ordinarily be set off in well-nourished normal humans (patients) to promote the human patient's ability to overcome tissue damage. The humans who would be beneficially treated by the therapy of this invention would be preselected prior to surgery since most normal humans would not require the therapy of this invention. In this invention a sufficient amount of LEM (leukocyte endogenous mediator, also sometimes known as leukocyte pyrogen, endogenous pyrogen, lymphocyte activating factor or Interleukin I) is parenterally administered to raise the body temperature of a human above normal and usually at least about 1° C. With this invention it is now possible to marshall the human's ability to minimize, by stimulating the human's metabolism, tissue damage, improve wound healing and reduce the susceptibility to infections, e.g., bacterial.

LEM (endogenous pyrogen) is a well known material. It may be classified as a hormone in that it appears to be a substance which is produced in one region of the body and transported to another region where it induces a specific bodily response. The isolation and various experiments with same have been reported in the scientific literature for many years. See:

Kampschmidt, R. F., Upchurch, H. F., Eddington, C. L. Pulliam, L. A. Multiple biological activities of a partially purified leukocytic endogenous mediator. *Am. J. Physiol.*, 224:530, 1973;

Kampschmidt, R. F. Leukocytic endogenous mediator. *J. Reticuloendothel Soc.*, 23:287, 1978;

Dinarello, C. A., Goldin, N. P., Wolff, S. M. Demonstration and characterization of two distinct human leukocyte pyrogens. *J. Exp. Med.*, 139:1369, 1974;

Bodel, P. Studies on the mechanism of endogenous pyrogen production. III. Human blood monocytes. *J. Exp. Med.*, 140:954, 1974;

Kaiser, H. K., Wood, W. B., Jr. Studies on the pathogenesis of fever: Role of endogenous pyrogen by polymorphonuclear leukocytes. *J. Exp. Med.*, 136:944, 1971;

Kampschmidt, R. F., Pulliam, L. A., Upchurch, H. F. Sources of leukocytic endogenous mediator in the rat. *Proc. Soc, Exp. Biol. Med.*, 144:882, 1973;

Bodel, P., Miller, H. Pyrogen from mouse macrophages causes fever in mice. *Proc. Soc. Exp. Biol. Med.*, 151:93, 1976;

Kampschmidt, R. F., Upchurch, H. F. Lowering of plasma iron concentrations in the rat with leukocytic extracts. *Am. J. Physiol.*, 216:1287, 1969;

Kampschmidt, R. F., Upchurch, H. F. The effect of endogenous pyrogen on the plasma zinc concentration of the rat. *Proc. Soc. Exp. Biol. Med.*, 134:1150, 1970;

Bornstein, D. L., Bredenberg, C., Wood, B. W. Studies on the pathogenesis of fever XI. Quantitative features of the febrile response to leukocytic pyrogen. *J. Exp. Med.*, 117:349, 1963;

Cheuk, S. F., Hahn, H. H., Moore, D. M., Krause, D. N., Tomasulo, P. A., Wood, W. B., Jr. Studies on the pathogenesis of fever. XX. Supression and regeneration of pyrogen-producing capacity of exudate granulocytes. *J. Exp. Med.*, 132:127, 1970;

Wannemacher, R. W., Jr., Pekarek, R. S., Beisel, W. R. Mediator of hepatic amino acid flux in infected rats. *Proc. Soc. Exp. Biol. Med.*, 139:128, 1972;

Eddington, C. L., Upchurch, H. F., Kampschmidt, R. F. Effect of extracts from rabbit leukocytes on levels of acute phase globulins in rat serum. *Proc. Soc. Exp. Biol. in Med.*, 126:159, 1971;

Kampschmidt, R. F., Upchurch, H. F. Possible involvement of leukocytic endogenous mediator in granulopoiesis. *Proc. Soc. Exp. Biol. Med.*, 155:89, 1977;

George, D. T., Abeles, F. B., Mapes, C. A., Sobocinski, P. Z., Zenser, T. V., Powanda, M. C. Effect of leukocytic endogenous mediators on endocrine pancreas secretory responses. *Am. J. Physiol.*, 223:E240, 1977;

Murphy, P. A., Simon, P. L., Willoughby, W. F. Endogenous pyrogens made by rabbit peritoneal exudate cells are identical with lymphycyte-activating factors made by rabbit alveolar macrophages. *J. Immunol*, 124:2498, 1980;

Rosenwasser, L. J., Dinarello, C. A., Rosenthal, A. S. Adherent cell function in murine T-lymphocyte antigen recognition. IV. Enhancement of murine T-cell antigen recognition by human leukocytic pyrogen. *J. Exp. Med.*, 150:709, 1979;and Moore, R. N., Oppenheim, J. J., Farrar, J. J., Carter, C. S., Jr., Waheed, A., Shadduck, R. K. Production of lymphocyte-activating factor (Interleukin 1) by macrophages activated with colony-stimulating factors. *J. Immunol.*, 125:1302, 1980.

BRIEF STATEMENT OF THE INVENTION

This invention is particularly directed to the parenteral administration of LEM, preferably human LEM, to a protein malnourished human who is to undergo surgery. It should be understood that animal produced LEM may be used in place of human LEM, or ultimately LEM produced genetically or synthetically as these technologies develop. The LEM administered should be sufficient to generate a rise in human body temperature of preferably at least about 1° C. The LEM will normally be administered for a period of time prior to the surgery, usually up to 24 hours prior, and after surgery to maintain elevated body temperature for 72 additional hours. In this manner, the patient's metabolism is stimulated by LEM to generate a fever and at the same time to cause one or more of the following to be mediated in the human's body:
1. reduced plasma concentrations of zinc and iron
2. increased plasma concentration of copper as ceruloplasmin
3. increased hepatic synthesis of the 'acute-phase' proteins:
   $\alpha_1$-antitrypsin, $\alpha_1$-acid glycoprotein,
   $\alpha_2$-macroglobulin, haptoglobin,
   C-reactive protein.
4. increased serum concentrations of insulin and glucagon
5. increased muscle protein breakdown and net catabolism
6. increased liver weight and protein content 7. redistribution of host protein from somatic to visceral tissues 8. increased blood glucose levels 9. reduced fasting ketonemia 10. increased prostaglandin production 11. increased lymphocyte proliferation in response to antigens 12. increased neutrophil lysozyme production 13. increased neutrophil superoxide production 14. increased production of colony stimulating factor (macrophage) 15. increased granulocytosis 16. increased release of immature granulocytes (band forms) from bone marrow The metabolic functions (1 through 16 listed above) are intimately beneficially involved in reducing tissue damage, promoting healing of wound damage and fighting secondary bacterial infections.

Thus with this invention the protein malnourished patient who normally is unable to generate sufficient endogenous LEM is able to better fight surgical tissue damage and survive secondary infection (e.g., reduce the incidence and severity of bacterial infections).

In order to use this invention the LEM may be parenterally administered, e.g., by injection such as intravenous, subcutaneous or intramuscular, or intravenous drip. The dosage would obviously vary; however, it is preferred that the dosage administered produce a prolonged 1° C. rise in patient (human) body temperature (e.g., one to four hours each six hour bolus IV administration). Preferably, the dosage of LEM is about 1–40 nanograms per kg of human body weight, and most preferably, 3–20 nanograms per kg of human body weight for a single dose injection every six hours. An intravenous drip for 24 hours would contain 4–150 nanograms per kg of human body weight per hour given continuously. However, it should be understood that additional LEM may be administered to further elevate body temperature 2° to 3° C. over normal depending upon the human.

As used herein, "surgery" refers to an operative procedure requiring general anesthesia and usually lasting more than 1 hour (e.g. colectomy, gastrectomy, thoracotomy).

As used herein it should be understood that the term LEM is intended to include pharmaceutically acceptable salts and acid-addition salts thereof, such as, for example, phosphates, chloride, acetic acid, and salts of bases such as for example barium hydroxide, sodium hydroxide.

The invention will now be illustrated with reference to the following examples. In the examples all temperatures are in degrees centigrade.

EXAMPLE 1 - Preparation of Human LEM

All glassware, materials, and reagents used in the procedure are sterile and endotoxin-free. 500 ml of anti-coagulated (citrate) venous human blood is allowed to sediment on a Ficoll-Hypaque gradient (Pharmacia, Inc., Stockholm, Sweden) at 9° C. The monocyte-rich fraction is then separated from erythrocytes and centrifuged at $900 \times g$ for 10 minutes. After removal of any remaining erythrocytes by brief exposure to hypotonic saline, the monocytes are washed with saline and 5% dextrose and then resuspended in Hanks' balanced salt solution containing 10 U/ml of sodium heparin, 150 mg/dl glucose, and 1000 U/ml of penicillin G (sodium salt). Approximately $1 \times 10^8$ monocytes are stimulated to produce LEM by incubation with $3 \times 10^9$ heat-killed *Staphylococcus albus* for 18 hours.

Briefly, *Staphylococcus albus* ($3 \times 10^9$ colony forming units) is added to phosphate buffered saline (pH 7.4) and heated to 100° C. for 30 minutes. The heat-killed bacteria are cooled to 37° C. and placed in a shaking water bath with the monocytes at a ratio of 30 heat-killed bacteria to one monocyte and the solution incubated at 37° for 18 hours.

After the 18 hour incubation, the bacteria and cells are removed by centrifugation at $3600 \times g$ for 30 min and the supernatant passed through a 0.45 micron filter (Millipore Corp., Bedford, Mass.) Aliquots of LEM are tested prior to purification for (1) endotoxin contamination with *Limulus* lysate assay (Pyrotell; Associates of Cape Cod, Falmouth, Mass.) and (2) bacterial contamination by culturing in thioglycollate medium at 37° C. for 48 hr.

Purification of Human LEM

The supernatant containing LEM is then diluted in ten volumes of sterile and pyrogen-free phosphate buffered saline (pH 7.4) and subjected to ultrafiltration across an anisotropic membrane fractioning at molecular weights of approximately 35,000–50,000 daltons (Amicon, Danvers, Mass.). The less than 50,000 dalton fraction containing LEM is dialyzed against a Tris buffer (pH 8.1) at 4° C. for 12 hours and is then applied to a DEAE-cellulose ion-exchange column (DEAE-cellulose, DE-52, Whatman Ltd., London, England). The LEM is eluted with a sodium chloride gradient in the first ten to twenty fractions at 3–5 mmhols. The resulting LEM is concentrated by lyophilization and is again tested for pyrogenicity and sterility by *Limulus* lysate assay and evidence of bacterial growth, respectively.

EXAMPLE 2 - Hypodermic Solutions For IV Bolus

The solution is compounded from the following:

| LEM | 1000 nanograms |
| Sodium chloride | 5 parts by volume |
| Double-distilled water q.s. ad | 500 parts by volume |
| Human serum albumin | 5 parts by volume |

The active ingredient LEM, human serum albumin and sodium chloride are dissolved in the distilled water; the solution is sterilized and made free from suspended particles by being filtered (0.22 micron), and is filled into a 5 cc-ampule which is sealed. The human serum albumin is added only to prevent adhesion of the LEM to glass and subsequently to plastic syringes and/or tubing. The contents of the ampule are an injectable dosage unit composition. For continuous intravenous administration, four vials of the solution of Example 2 are injected each hour into a 0.5% saline solution (drip) normally used for IV administration.

EXAMPLE 3

A protein malnourished patient (human) 70 kg man is administered by IV bolus injection, 1000 nanograms of LEM three hours prior to major surgery (e.g., gastrectomy) and an IV drip providing 4000 nanograms of LEM per hour for a period of three days after surgery. The human is monitored for temperature elevation and the IV drip adjusted to maintain human body temperature to about 1° C. over normal.

The amount of active ingredient in these illustrative examples may be varied to achieve the dosage unit range set forth above, and the amounts and nature of the inert pharmaceutical carrier ingredients may be varied to meet particular patient requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

What is claimed is:

1. The method of preparing a protein malnourished human for surgery comprising parenterally administering to a protein malnourished human prior to said surgery a sufficient amount of LEM to raise the body temperature of the protein malnourished human above normal during at least some of the time the protein malnourished human is undergoing surgery.

2. The method of claim 1 in which LEM is administered intravenously.

3. The method of claim 1 in which the LEM is administered in the form of a sterile injectable preparation or sterile intravenous drip.

4. The method of claim 1 in which the patient has a serum albumin less than about 3.2 gm/dl.

5. The method of claim 1 in which the amount of LEM administered is sufficient to raise the human's body temperature at least one degree centigrade.

6. The method of claim 1 in which the LEM is administered about three hours prior to surgery.

7. The method of treating a protein malnourished patient who is to undergo surgery which comprises the parenteral administration of LEM to said protein malnourished human in an amount sufficient to raise the body temperature of the protein malnourished human above normal during the time the surgery is taking place and for a period of time after surgery is completed.

8. The method of claim 7 in which the LEM is administered in the form of a sterile injectable preparation or sterile intravenous drip.

9. The method of claim 7 in which the amount of LEM administered is sufficient to raise the human's body temperature at least about one degree centigrade.

10. The method of claim 7 in which the human has a serum albumin less than about 3.2 gm/dl.

* * * * *